US011852580B2

(12) United States Patent
Vicet et al.

(10) Patent No.: US 11,852,580 B2
(45) Date of Patent: Dec. 26, 2023

(54) CAPACITIVE SENSOR FOR PHOTOACOUSTIC SPECTROSCOPY, DEVICE AND METHOD USING SUCH A SENSOR

(71) Applicants: UNIVERSITE DE MONTPELLIER, Montpellier (FR); CENTRE NATIONAL DE LA RECHERCHE SCIENTIFIQUE, Paris (FR)

(72) Inventors: Aurore Vicet, Prades-le-Lez (FR); Kaim Chamassi, Montpellier (FR); Michaël Bahriz, Montpellier (FR)

(73) Assignees: UNIVERSITE DE MONTPELLIER, Montpellier (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 294 days.

(21) Appl. No.: 17/295,137

(22) PCT Filed: Nov. 20, 2019

(86) PCT No.: PCT/EP2019/081911
§ 371 (c)(1),
(2) Date: May 19, 2021

(87) PCT Pub. No.: WO2020/104518
PCT Pub. Date: May 28, 2020

(65) Prior Publication Data
US 2022/0018758 A1  Jan. 20, 2022

(30) Foreign Application Priority Data
Nov. 21, 2018 (FR) ........................... 1871680

(51) Int. Cl.
*G01N 21/17* (2006.01)
*B06B 1/02* (2006.01)
*G01N 33/00* (2006.01)

(52) U.S. Cl.
CPC ....... *G01N 21/1702* (2013.01); *B06B 1/0292* (2013.01); *G01N 33/0047* (2013.01);
(Continued)

(58) Field of Classification Search
CPC .......... G01N 21/1702; G01N 21/1704; G01N 21/1706; G01N 21/00; G01N 2021/1704; G01N 2201/06113
See application file for complete search history.

(56) References Cited

U.S. PATENT DOCUMENTS

| | | |
|---|---|---|
| 6,344,647 B1 | 2/2002 | Jourdain et al. |
| 2012/0227498 A1 | 9/2012 | Kandori et al. |

(Continued)

FOREIGN PATENT DOCUMENTS

WO  2017/186796 A1  11/2017

OTHER PUBLICATIONS

International Search Report and Written Opinion received in PCT/EP2019/081911, dated Jan. 15, 2020.
(Continued)

*Primary Examiner* — Suman K Nath
(74) *Attorney, Agent, or Firm* — Greer, Burns & Crain, Ltd

(57) ABSTRACT

A sensor for photoacoustic spectroscopy including a support and a mechanical resonator fastened to the support, including at least one sensor element designed to be vibrated by an acoustic wave, and at least one first capacitive electrode mechanically coupled to the sensor element so as to be moved by the sensor element when it is vibrated; and at least one second capacitive electrode forming with the at least one
(Continued)

first electrode, a capacitive sensor; the support facing the sensor element, an apertured part formed by one or more through-openings. Also provided is a detection and/or measurement device and method, for photoacoustic spectroscopy, using such a sensor.

14 Claims, 3 Drawing Sheets

(52) U.S. Cl.
CPC ............... *G01N 2021/1704* (2013.01); *G01N 2201/062* (2013.01); *G01N 2201/06113* (2013.01)

(56) References Cited

U.S. PATENT DOCUMENTS

2016/0202225 A1* 7/2016 Feng .................... G01N 29/022
422/90
2017/0289702 A1* 10/2017 Inoue .................... H04R 19/04

OTHER PUBLICATIONS

French Search Report received in Application No. 1871680, dated Jul. 10, 2019.

* cited by examiner

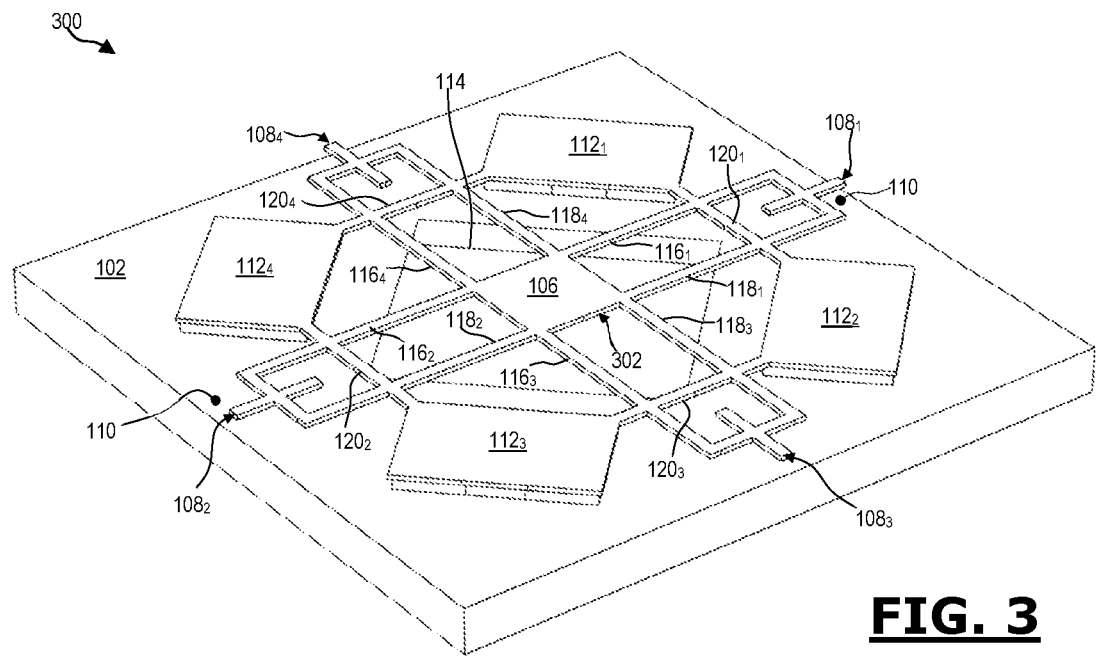
FIG. 3
FIG. 4
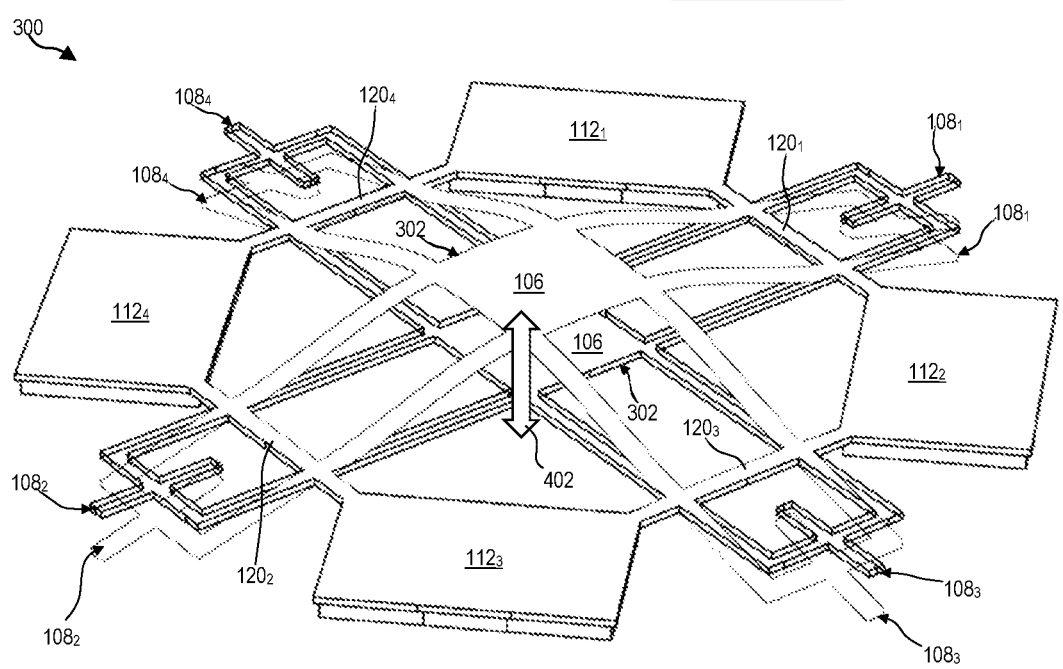

CAPACITIVE SENSOR FOR PHOTOACOUSTIC SPECTROSCOPY, DEVICE AND METHOD USING SUCH A SENSOR

BACKGROUND

The present invention relates to a capacitive sensor for photoacoustic spectroscopy, in particular photoacoustic spectroscopy of gases. It also relates to a detection and/or measurement device and a method using such a sensor.

The field of the invention is the field of photoacoustic spectroscopy sensors, and in particular sensors for photoacoustic spectroscopy of gases.

In the infrared, certain gases have light absorption bands. This characteristic is used in photoacoustic spectroscopy to detect these gases, or to measure the concentration of these gases.

In summary, a laser modulated to a given frequency illuminates a gas. The laser is absorbed by this gas and causes a localized heating of the gas. As the intensity of the laser is modulated, the localized heating of the gas is also modulated. The modulation of the heating translates into the creation of a sound wave of the same frequency as the modulation frequency. This sound wave can then be detected by a photoacoustic spectroscopy sensor.

A first type of photoacoustic sensor is in the form of an acoustic resonance chamber equipped with a microphone. This first type of sensor requires the use of a resonance chamber in order to increase the signal-to-noise ratio.

A second type of photoacoustic sensor is in the form of a piezoelectric resonator sensor. Such a sensor makes it possible to dispense with an acoustic chamber but still remains complex, not very compact and not very easy to integrate.

Moreover, no capacitive sensor for photoacoustic spectroscopy currently exists. In fact, the damping effect, also known by the name "squeeze film" has always constituted a stumbling block for the design of capacitive sensors for photoacoustic spectroscopy. In fact, the detection sensitivity depends on the proximity and the size of the capacitive electrodes. But, the damping effect increases with the proximity and the size of the electrodes and degrades the detection sensitivity.

An aim of the present invention is to overcome these drawbacks.

Another aim of the invention is to propose a capacitive sensor for photoacoustic spectroscopy.

Another aim of the invention is to propose a capacitive sensor for photoacoustic spectroscopy having better sensitivity than the current sensors.

It is also an aim of the present invention to propose a capacitive sensor for photoacoustic spectroscopy that is more compact than the current sensors, and/or that can be integrated.

SUMMARY

The invention makes it possible to achieve at least one of these aims with a sensor for photoacoustic spectroscopy, in particular photoacoustic spectroscopy of gases, comprising:
- a support,
- a mechanical resonator, fastened to said support, and comprising:
  - at least one sensor element intended to be vibrated by an acoustic wave, and
  - at least one first capacitive electrode, mechanically coupled to said sensor element, so as to be moved by said sensor element when it is vibrated; and
- at least one second capacitive electrode forming, with said at least one first electrode, a capacitive sensor.

Thus, the invention proposes a capacitive sensor for photoacoustic spectroscopy, in particular photoacoustic spectroscopy of gases, in which the acoustic wave sensor element is separated from the capacitive electrodes used for the capacitive measurement. Thus, in the sensor according to the invention, it is possible to envisage different architectures, on the one hand for capturing the sound wave at the level of the sensor element, and on the other hand for capacitive detection at the level of the capacitive electrodes. It is then possible to adopt, at the level of the sensor element, a specific architecture limiting, or reducing, the squeeze film damping effect, but without affecting the capacitive measurement. Similarly, it is possible to adopt, at the level of the capacitive electrodes, a specific architecture increasing the sensitivity of the capacitive detection, without affecting the squeeze film damping effect at the level of the sensor element. The sensor according to the invention thus allows a greater measurement sensitivity compared with the current sensors.

In addition, the capacitive detection technology allows on the one hand an architecture that is more compact compared with the current sensors, and on the other hand production of the sensor according to the invention in the form of an integrated component.

The capacitive technology makes it possible to produce the sensor according to the invention by means of a doped silicon technology, without a step of implanting or depositing a metallic film, which makes it possible to increase the quality factor of the resonator and to reduce the cost and the complexity of manufacture.

Generally, in order to obtain a capacitive sensor for photoacoustic spectroscopy having good sensitivity, the variation of the capacitance must be significant. In order to obtain such a capacitance variation, it is necessary:
- on the one hand for the surface sensitive to the sound wave to be large; and
- on the other hand for the distance separating the capacitive measurement capacitors to be as small as possible.

Satisfying both of these conditions involves adding a large viscous damping between the capacitors mainly because there is a thin film of air between the capacitors. It is this contradiction which dissuades a person skilled in the art from using a capacitive sensor for photoacoustic spectroscopy.

As explained above, the present invention makes it possible to avoid this contradiction by separating, in the resonator, the part used to capture the acoustic wave, namely the sensor element, from the part used for the capacitive measurement, namely the first capacitive electrode.

According to an embodiment, the mechanical resonator, and more generally the sensor, defines a general plane. According to an embodiment example, the thickness of the sensor can be less than or equal to 400 µm, or even 600 µm.

Advantageously, the mechanical resonator can be arranged to be made to move by the sound wave in a direction vertical to the general plane of the sensor, and/or of the resonator.

Thus, the displacement amplitude of the resonator, and in particular of the sensor element, is increased.

According to a particularly preferred embodiment, at least one, in particular each, first capacitive electrode is offset/shifted with respect to the sensor element in a direction perpendicular to the direction of displacement of the sensor element, and/or in a direction located in the general plane of the sensor and/or of the resonator.

The sensor element can have any geometric shape, such as for example the shape of a square, circle, triangle, etc.

According to an embodiment example, the sensor element has a solid, or unperforated, surface.

According to the invention, the, or each, first capacitive electrode is mobile.

The first capacitive electrode can have any geometric shape, such as for example the shape of a cross, rectangle, etc.

Advantageously, the sensor element can have a larger surface area compared with the surface area of at least one, in particular each, first capacitive electrode.

Thus, the capture of the sound wave by the sensor element is improved, while reducing the damping effect at the level of the first electrode.

Advantageously, the resonator can have a quality factor greater than or equal to 10.

Such a quality factor makes it possible to improve the selectivity of the sensor according to the invention.

According to a particularly advantageous embodiment, the support has a hollowed-out or perforated part opposite the sensor element.

Thus, the sensor according to the invention reduces, or even cancels out, any damping effect of the sensor element during its mechanical oscillation, which increases the movement amplitude of the sensor element and consequently the sensitivity of said sensor.

The perforated part can be formed by a single through hole or not.

Alternatively, the perforated part can be formed by several through holes or not.

Advantageously, the resonator can comprise several first electrodes mechanically coupled to the sensor element and moved by the sensor element.

The use of a larger number of electrodes makes it possible to increase the sensitivity of the capacitive detection while making it possible to customize the architecture of the resonator and thus of the sensor.

When the resonator comprises several first electrodes, it is important that said electrodes are synchronized with one another for capacitive measurement so as to keep the electrical signals generated by said electrodes in phase.

In particular, the resonator can comprise four first capacitive electrodes aligned in pairs with the sensor element, in particular in two directions perpendicular to one another, so as to form a cross centered on the sensor element.

Such an architecture of the resonator makes it possible to improve the capacitive detection through the use of several first capacitive electrodes, while preserving mechanical equilibrium for the mechanical resonator.

Preferably, the resonator can be fastened to the support at the level of at least one mechanical vibration node.

Thus, the losses caused by the fastening of the resonator on the support are limited, or even cancelled out.

A vibration node is defined as being a zone where the displacements and the mechanical stresses are zero, or close to zero.

For at least one first capacitive electrode, it is possible to fasten the resonator to the support at the level of a fastening position which is not located between the sensor element and said first capacitive electrode.

Alternatively, for at least one first capacitive electrode, the resonator can be fastened to the support at a fastening position located between the sensor element and said first capacitive electrode.

This fastening position can be selected so that the mechanical movements of the sensor element and of the first capacitive electrode are either:
 in the same direction;
 or in opposite directions, so that when the sensor element is displaced in one direction, said first capacitive electrode is displaced in the other direction.

Such an architecture makes it possible to use the fastening as a lever in order to adjust the movement of the first capacitive electrode.

More particularly, for at least one first capacitive electrode, the fastening position can be closer to the sensor element than to said first capacitive electrode.

Thus, such a fastening can be used as a lever to amplify the amplitude of the movements of said first measurement electrode. Thus, the accuracy of the capacitive detection produced by this electrode can be increased.

Advantageously, the resonator can be produced in a single piece, in particular from one and the same material.

More particularly, the resonator can be produced by machining of one and the same layer of a material, such as a layer of silicon, or any other electrically conductive material.

Advantageously, at least one first capacitive electrode can be integral with the sensor element through at least one linking arm having a width that is smaller than that of the sensor element.

Thus, the damping effect caused by the fastening arm between the sensor element and the first electrode is reduced.

According to a particularly advantageous characteristic, at least one first capacitive electrode can be perforated or have holes.

Thus, air can pass through said first electrode, which reduces the damping effect which can exist when said first capacitive electrode is made to move.

According to a preferred embodiment example, at least one first electrode can be formed by several parallel branches, at a distance from one another.

Such an architecture makes it possible to reduce the damping effect. In addition, such an architecture also makes it possible to have a weak series resistance and to keep a good sensitivity on the electrical signal.

Each branch can have a negligible width, for example approximately ten micrometers.

According to an embodiment, the, or each, second capacitive electrode can be fixed.

According to an embodiment, at least one, in particular each, second electrode can be arranged on/in the support, opposite the, or a, first capacitive electrode.

According to an embodiment example, the sensor according to the invention can have, for at least one first capacitive electrode, a second capacitive electrode that is individual for said first capacitive electrode.

Alternatively, or in addition, the sensor according to the invention can have a second capacitive electrode common to several, and in particular to all, of the first capacitive electrodes.

According to an advantageous characteristic, the sensor according to the invention can be produced from a structure constituted by a stack of layers of a conductive material and insulating material.

The structure can comprise two conductive layers separated by a sacrificial insulating layer.

In this case, the resonator can be produced from a first conductive layer and the second capacitive electrode can be constituted by, or produced from, a second conductive layer.

For example, the conductive material can be silicon and the insulating material can be SiO2 and the structure can be a structure of silicon on insulator having at least two layers of silicon.

Of course, the sensor according to the invention can also comprise contacts or electrical tracks to electrically polarize the first and second capacitive electrodes.

According to a non-limitative embodiment example, the sensor can comprise an electrical contact at the level of at least one fastening of the resonator to the support, in order to polarize the first electrode or electrodes with a ground potential, or with a voltage different from a ground potential.

In addition, as explained above, the resonator can be produced in a single piece from one and the same material.

In other words, the set formed by the sensor element and the at least one first capacitive electrode is produced in a single piece and from a single material.

In this case, the sensor element also forms a capacitive electrode linked or connected to each first capacitive electrode and contributes to in the capacitive measurement by being polarized by electrical charges injected into each first capacitive electrode.

According to another aspect of the same invention, a detection and/or measurement device for photoacoustic spectroscopy, in particular of air, is proposed comprising:
at least one light source emitting a modulated light radiation; and
at least one sensor according to the invention.

The device according to the invention can comprise several modulated light sources.

At least two light sources can be modulated at one and the same modulation frequency, or at different frequencies.

The device according to the invention can comprise at least two light sources emitting light radiations of different wavelengths.

It is thus possible, with one and the same device, to detect different gases, or to measure the quantity of different gases, absorbing different wavelengths, or also to differentiate between two gases having very similar absorption spectra.

The modulation frequency of at least one light source can also be adjustable.

In order to increase the measurement sensitivity, the light source or sources can be focused on a point located opposite the sensor element. Thus, the sound wave can be generated opposite the sensor element and its capture by the sensor element can be improved.

At least one light source can be a laser source emitting a laser radiation.

Alternatively, or in addition, at least one light source can be, or can comprise:
at least one light emitting diode;
at least one resonant cavity light emitting diode;
at least one RCLED the emission spectrum of which is much narrower than that of a traditional infrared LED.

According to another aspect of the same invention, a method for detecting a gas, and/or measuring the concentration of a gas, is proposed, using:
a sensor according to the invention; or
a device according to the invention.

In particular, in order to carry out detection or measurement of a gas, the sensor according to the invention, or the device according to the invention, is immersed in an environment containing said gas.

Generally, the invention can be used for any application requiring a gas sensor.

For example, the invention can be implemented to detect:
methane ($CH_4$) with a laser emitting at 1.6 µm or at 2.3 µm or also at 3.3 µm;
ethylene ($C_2H_4$) with a laser emitting at 3.25 µm.

The invention can be used for detection:
for analyzing the chemical composition of gases for engine applications, for example for fuels or exhaust gases in the automotive field;
for monitoring volatile organic compounds, in particular in the environmental field for monitoring BTEX (benzene, toluene, ethylbenzene, xylenes);
for analyzing exhaled air, in particular in the medical field for prevention and aiding medical diagnosis;
for monitoring manufacturing processes in the industrial field;
for quality and ripening control of products, in particular in the agri-food field.

BRIEF DESCRIPTION OF THE DRAWINGS

Other advantages and characteristics will become apparent on examination of the detailed description of an embodiment which is in no way limitative, and the attached drawings, in which:

FIGS. 3 and 4 are diagrammatic representations of a second embodiment example of a sensor according to the invention;

DETAILED DESCRIPTION

It is of course understood that the embodiments that will be described hereinafter are in no way limitative. In particular, variants of the invention can be imagined comprising only a selection of the characteristics described hereinafter, in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In the figures, elements common to several figures keep the same reference.

Figure 1:
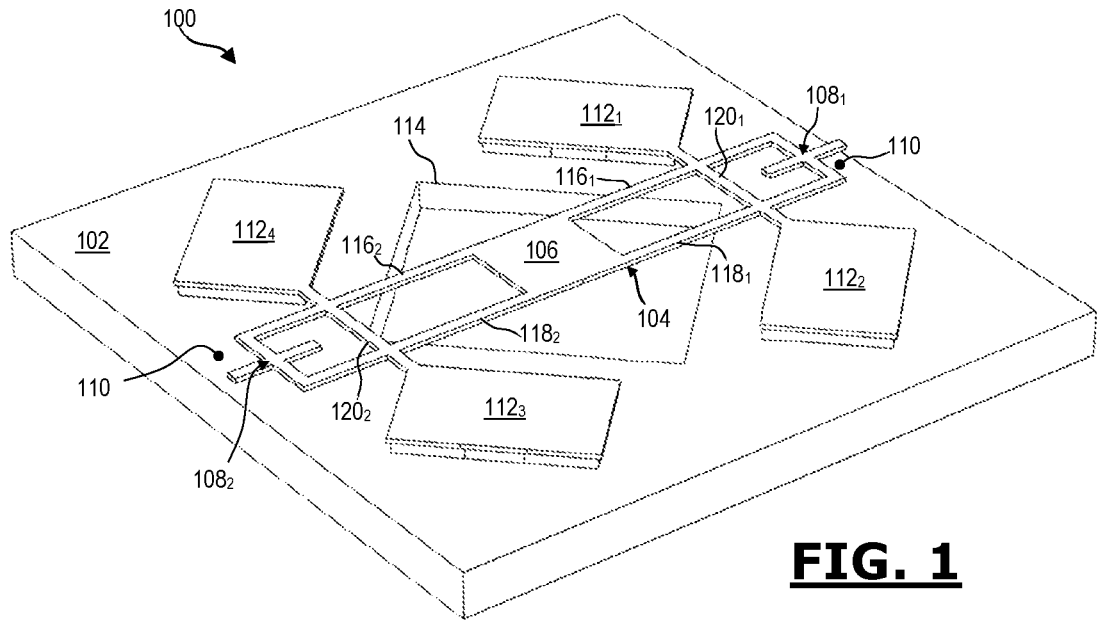
FIGS. 1 and 2 are diagrammatic representations of a first non-limitative embodiment example of a sensor according to the invention.

FIG. 1 is a diagrammatic representation of a first non-limitative embodiment example of a sensor according to the invention.

The sensor 100, shown in FIG. 1, comprises a support 102.

The sensor 100 comprises a mechanical resonator 104, intended to enter into mechanical resonance at its resonant frequency, under the effect of a sound wave.

The mechanical resonator 104 comprises a sensor element 106 on which a sound wave is exerted to set the whole of the resonator 104 in resonance.

The mechanical resonator 104 also comprises at least one first capacitive electrode that is offset and separated from the sensor element, and mechanically coupled to the sensor element so that it is moved by the sensor element 106 when it is made to move. In the example shown in FIG. 1, the mechanical resonator 104 comprises two first electrodes $108_1$ and $108_2$, mechanically coupled to the sensor element 106, positioned on either side of the sensor element, and aligned with the sensor element 104.

The sensor 100 comprises a second capacitive electrode 110, common to the two first capacitive electrodes $108_1$ and $108_2$, and forming a capacitive sensor with each of said first capacitive electrodes $108_1$-$108_2$. In the example shown in FIG. 1, the second capacitive electrode 110 is formed by the whole of the support 102. To this end, the support 102 is made of an electrically conductive material.

The sensor 100 comprises fastening blocks $112_1$-$112_4$, to make the resonator 104 integral with the support 102 at the level of the two oscillation nodes of said resonator 104.

The support 102 has an entirely perforated part 114 at the level of, and opposite, the sensor element 106. This perforated part 112 allows air to circulate so as to avoid the formation of a layer of air between the sensor element 106 and the support 102, which could damp the movement of the sensor element during its oscillation under the effect of the sound wave.

The sensor element 106 is linked to the first capacitive electrode $108_1$ by two parallel linking arms $116_1$ and $118_1$, having a very narrow width compared with that of the sensor element 106 and being at a distance from one another. Similarly, the sensor element 106 is linked to the second capacitive electrode $108_2$ by two parallel linking arms $116_2$ and $118_2$, having a very narrow width compared with that of the sensor element 106 and being at a distance from one another.

Thus, the link between the sensor element 104 and the first capacitive electrodes $108_1$-$108_2$ is not affected by a damping effect during the mechanical oscillation of the resonator 104.

In addition, the resonator 104 comprises a first branch $120_1$, called fastening branch, making it possible to fasten the resonator 104 to the fastening blocks $112_1$-$112_2$. This fastening branch $120_1$ creates a fastening line located at the level of an oscillation node between the sensor element 106 and the first capacitive electrode $108_1$. This fastening branch $120_1$ is held in a mobile manner, on either side, in the blocks $112_1$-$112_2$.

Similarly, the resonator 104 comprises a second branch $120_2$, called fastening branch, making it possible to fasten the resonator 104 to the fastening blocks $112_3$-$112_4$. This fastening branch $120_2$ creates a fastening line located at the level of an oscillation node between the sensor element 106 and the first capacitive electrode $108_2$. This fastening branch $120_2$ is held in a mobile manner, on either side, in the blocks $112_3$-$112_4$.

In the sensor 100 in FIG. 1, the first capacitive electrodes $108_1$-$108_2$ are identical.

In the example shown in FIG. 1, each first capacitive electrode $108_1$-$108_2$, has two branches, perpendicular to one another so as to form a cross or a "+".

Such an architecture makes it possible to limit the damping effect at the level of each of these electrodes, while bringing each of the first capacitive electrodes $108_1$-$108_2$ as close as possible to the second capacitive electrode 110.

In addition, each first capacitive electrode $108_1$-$108_2$ is polarized to a non-zero electrical potential by electrical contacts (not shown) at the level of the fastening blocks $112_1$-$112_4$. The electrical potential is propagated in the whole of the resonator, and in particular in the first capacitive electrodes $108_1$-$108_2$ due to the fastening branches $120_1$-$120_2$ held in the fastening blocks $112_1$-$112_4$.

In the example shown, the sensor element 106 and the first capacitive electrodes $108_1$-$108_2$ are produced in a single piece/layer. More generally, the whole of the resonator is produced in a single piece/layer.

As can be seen in FIG. 1, the sensor 100 defines a general plane.

The sensor element 106 is intended to capture a sound wave in the direction perpendicular to the principal plane of the sensor 100. The sensor element 106, and more generally the resonator 104, is intended to be deformed in the direction perpendicular to the principal plane.

The first electrodes $108_1$-$108_2$ are separated/shifted from the sensor element 106 in the principal plane of the sensor, or at least in a direction perpendicular to the direction in which the sensor element moves under the effect of an acoustic wave.

Figure 2:
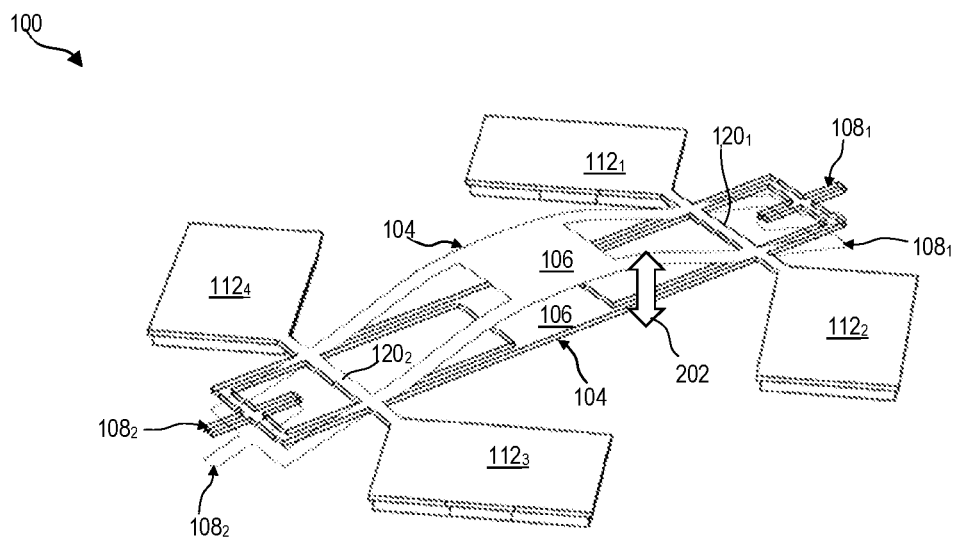

FIG. 2 is a representation of the sensor in FIG. 1, without the support 102.

In FIG. 2, the resonator 104 is shown in a rest state, and in a state of deformation under the effect of a sound wave.

As explained above, the sensor element, and more generally the resonator, is made to move in the direction indicated by the double arrow 202, perpendicular to the plane of the sensor, which is also the plane of the resonator 104 when it is at rest.

FIG. 2 clearly shows the sensor element 106 the movement of which moves each of the first capacitive electrodes $108_1$-$108_2$. The direction of movement of the sensor element 106 is opposite to that of the first capacitive electrodes $108_1$-$108_2$.

In addition, the resonator has a displacement that is zero, or almost zero, at the level of the fastening branches $120_1$-$120_2$, which correspond to oscillation nodes.

FIG. 3 is a diagrammatic representation of a second non-limitative embodiment example of a sensor according to the invention.

The sensor 300, shown in FIG. 3, comprises all of the elements of the sensor 100 in FIG. 1.

The sensor 300 comprises a resonator 302 which comprises all of the elements of the resonator 104 of the sensor 100 in FIG. 1.

The resonator 302 comprises, in addition to the elements of the resonator 104, two other first electrodes $108_3$-$108_4$, positioned on either side of the sensor element 106.

The first electrodes $108_3$-$108_4$ are aligned with the sensor element 106 in a direction different from that formed by the first electrodes $108_1$-$108_2$ with the sensor element 106. Thus, the first electrodes $108_1$-$108_2$ and the first electrodes $108_3$-$108_4$ form a cross at the center of which the sensor element 106 is located. In particular, the branches of the cross thus formed are perpendicular to one another.

The first capacitive electrodes $108_3$ and $108_4$ are identical to the first electrodes $108_1$ and $108_2$.

The sensor element 106 is linked to the first capacitive electrode $108_3$ by two parallel linking arms $116_3$ and $118_3$, having a very narrow width compared with that of the sensor element 106 and being at a distance from one another. Similarly, the sensor element 106 is linked to the first capacitive electrode $108_4$ by two parallel linking arms $116_4$ and $118_4$, having a very narrow width compared with that of the sensor element 106 and being at a distance from one another.

In addition, the resonator 104 comprises a third branch $120_3$, called fastening branch, making it possible to fasten the resonator 104 to the fastening blocks $112_2$-$112_3$. This fastening branch $120_3$ creates a fastening line located at the level of an oscillation node between the sensor element 106 and the first capacitive electrode $108_3$. This fastening branch $120_3$ is held in a mobile manner, on either side, in the blocks $112_2$-$112_3$.

Similarly, the resonator 104 comprises a fourth branch $120_4$, called fastening branch, making it possible to fasten the resonator 104 to the fastening blocks $112_4$-$112_1$. This fastening branch $120_4$ creates a fastening line located at the level of an oscillation node between the sensor element 106 and the first capacitive electrode $108_4$. This fastening branch $120_4$ is held in a mobile manner, on either side, in the blocks $112_4$-$112_1$.

Thus, the resonator 302 comprises four identical first capacitive electrodes $108_1$-$108_4$.

FIG. 4 is a representation of the sensor in FIG. 3, without the support 102.

In FIG. 4, the resonator 302 is shown in a rest state, and in a state of deformation under the effect of a sound wave.

As explained above, the sensor element 106, and more generally the resonator 302 is made to move in the direction indicated by the double arrow 402, perpendicular to the plane of the sensor 300, which is also the plane of the resonator 302 when it is at rest.

FIG. 4 clearly shows the sensor element 106 the movement of which moves each of the first capacitive electrodes $108_1$-$108_4$. The direction of movement of the sensor element 106 is opposite to that of the first capacitive electrodes $108_1$-$108_4$.

In addition, the resonator has a displacement that is zero, or almost zero, at the level of the fastening branches $120_1$-$120_4$, which correspond to oscillation nodes.

In the examples described, the sensor comprises a single second capacitive electrode formed by the support.

Alternatively, the second capacitive electrode 110 can be formed by a layer, or a track, of conductive material deposited on the support 102, or provided in the thickness of the support 102, or deposited under the support 102.

Alternatively, or in addition, the sensor 100 can comprise several second capacitive electrodes, in particular a second capacitive electrode that is individual for each first capacitive electrode.

Figure 5:
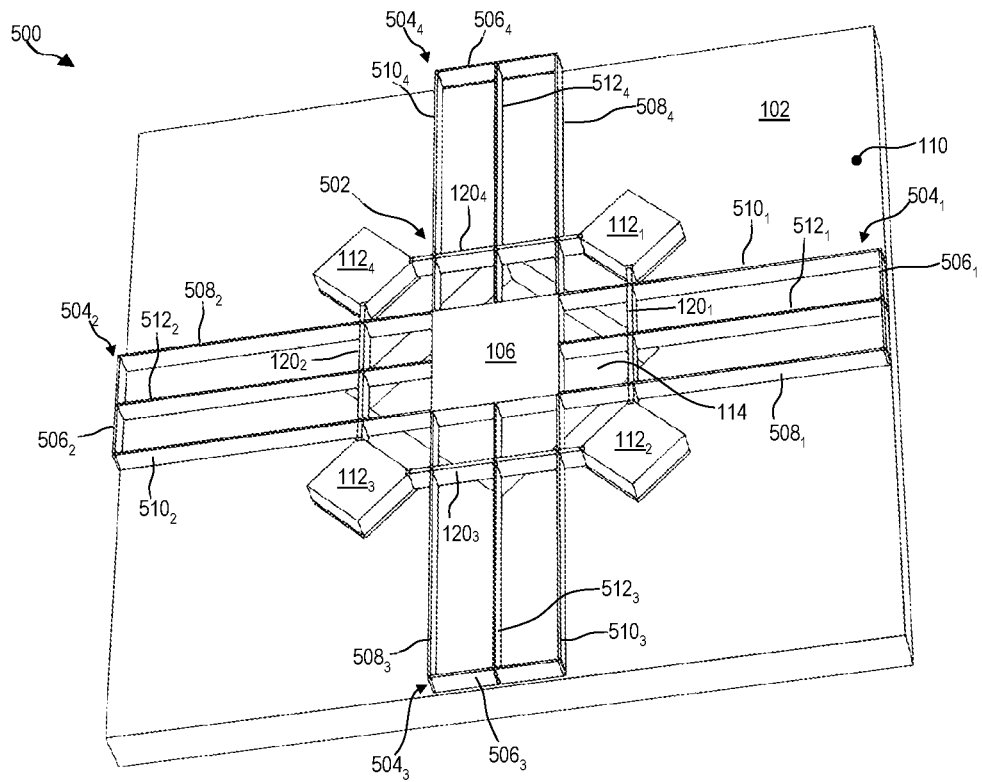
FIG. 5 is a diagrammatic representation of a third embodiment example of a sensor according to the invention.

FIG. 5 is a diagrammatic representation of a third non-limitative embodiment example of a sensor according to the invention.

The sensor 500, shown in FIG. 5, comprises the support 102 serving as second capacitive electrode 110, and having the perforated part 114.

The sensor 500 also comprises a resonator 502 comprising the sensor element 106 opposite the perforated part 114. The resonator 502 is fastened to the support 102 with the fastening blocks $112_1$-$112_4$, thanks to the fastening branches $120_1$-$120_2$ held in the fastening blocks $112_1$-$112_4$, and each positioned at the level of a vibration node of the resonator 502.

The resonator 502 comprises four identical first capacitive electrodes $504_1$-$504_4$, having a shape different from that of the electrodes $108_1$-$108_4$.

In particular, each first capacitive electrode $504_i$, with i=1 . . . 4, is formed by a distal branch $506_i$ linked to the sensor element 106 by three branches $508_i$, $510_i$ and $512_i$, parallel to one another, and perpendicular to the distal branch $506_i$. For example, the first capacitive electrode $504_1$ is formed by a distal branch $506_1$ linked to the sensor element 106 by three branches $508_1$, $510_1$ and $512_1$, parallel to one another, and perpendicular to the distal branch $506_i$. The width of each of the branches $506_i$, $508_i$, $510_i$ and $512_i$ is very narrow, of the order of approximately ten micrometers.

In addition, it should be noted that the fastening branches $120_1$-$120_2$ are each located on a vibration node, in a position closer to the sensor element than distal branches $506_1$-$506_4$ forming part of the first capacitive electrodes $504_1$-$504_4$. This architecture makes it possible to create a lever effect amplifying the mechanical movement of the first capacitive electrodes $504_1$-$504_4$. Thus, the sensitivity of the sensor 500 is improved.

Figure 6:
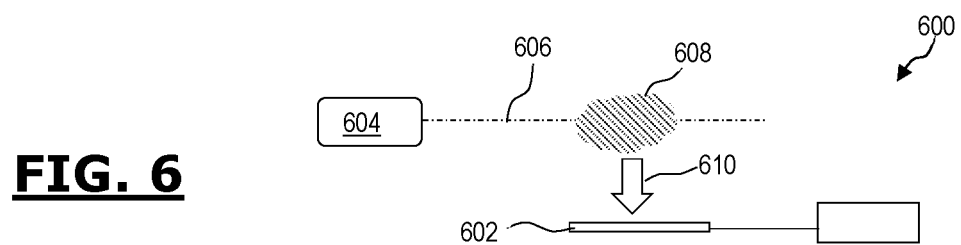
FIG. 6 is a diagrammatic representation of the device according to the invention.

FIG. 6 is a representation of a non-limitative embodiment example of a detection and/or measurement device according to the invention.

The device 600 in FIG. 6 comprises a sensor 602, which can be any one of the sensors 100, 300 or 500 in FIGS. 1-5.

The device 600 also comprises a laser source 604 emitting a laser radiation 606 modulated to a given modulation frequency and a given wavelength in the direction of a gaseous environment 608.

The modulation frequency can be comprised between 1 and 100 kHz, and in particular between 10 and 50 kHz.

The modulated laser radiation 606 is absorbed by the gas 608, which in response emits a sound wave 610 which is detected by the sensor 602.

The device 600 also comprises detection electronics for on the one hand polarizing the capacitive electrodes of the sensor 602 and on the other hand measuring an electrical signal representative of the capacitive detection.

In the example shown, the detection/measurement device comprises a single modulated laser source.

Alternatively, the device can comprise several laser sources emitting modulated laser radiations, at one and the same frequency, but having different wavelengths.

Alternatively or in addition, the device can comprise a light source which is not a laser source. For example, the device can comprise at least one light emitting diode, at least one resonant cavity light emitting diode, and at least one RCLED the emission spectrum of which is much narrower than a traditional infrared LED.

Advantageously, but non-limitatively, each mechanical resonator 104, 302 and 502 is produced in a single piece from one and the same material. In other words, in each mechanical resonator:
- the sensor element 106,
- the first capacitive electrodes, and
- the linking branches linking the sensor element and each first capacitive electrode;
- are produced in a single piece and from one and the same material. As a result, the sensor element and the linking branches also behave like a capacitive sensor linked or connected to each first capacitive electrode.

Of course, the invention is not limited to the examples detailed above.

The invention claimed is:

1. A sensor for photoacoustic spectroscopy comprising:
   a support;
   a mechanical resonator, fastened to said support, and including:

at least one sensor element intended to be vibrated by an acoustic wave, and at least one first capacitive electrode, mechanically coupled to said sensor element, so as to be moved by said sensor element when it is vibrated;

at least one second capacitive electrode forming, with said at least one first electrode, a capacitive sensor; and said support has, opposite to said at least one sensor element of said mechanical resonator, a perforated part formed by one or more through holes;

wherein said mechanical resonator is produced in a single piece.

2. The sensor according to claim 1, characterized in that the resonator comprises several first electrodes mechanically coupled to the sensor element and moved by said sensor element.

3. The sensor according to claim 1, characterized in that the resonator comprises four first capacitive electrodes aligned in pairs with the sensor element, so as to form a cross centered on the sensor element.

4. The sensor according to claim 1, characterized in that the resonator is fastened to the support at the level of at least one mechanical vibration node.

5. The sensor according to claim 1, characterized in that, for at least one first capacitive electrode, the resonator is fastened to the support at a fastening position located between the sensor element and said first capacitive electrode.

6. The sensor according to claim 5, characterized in that, for at least one first capacitive electrode, the fastening position is closer to the sensor element than said first capacitive electrode.

7. The sensor according to claim 1, characterized in that at least one first capacitive electrode is integral with the sensor element through at least one linking arm having a width that is smaller than that of the sensor element.

8. The sensor according to claim 1, characterized in that at least one first capacitive electrode is formed by several branches, having a negligible width, at a distance from one another.

9. The sensor according to claim 1, characterized in that at least one, in particular each, second electrode is arranged on/in the support, opposite the, or a, first capacitive electrode.

10. The sensor according to claim 1, characterized in that it is produced from a structure constituted by a stack of layers of a conductive material and insulating material.

11. A detection and/or measurement device for photoacoustic spectroscopy comprising:

at least one light source emitting a modulated light radiation; and at least one sensor according to claim 1.

12. The device according to claim 11, characterized in that the modulation frequency of at least one light source is adjustable.

13. Use of a device according to claim 11 for detecting a gas, and/or measuring the concentration of a gas.

14. Use of a sensor according to claim 1 for detecting a gas, and/or measuring the concentration of a gas.

* * * * *